Figure 1:
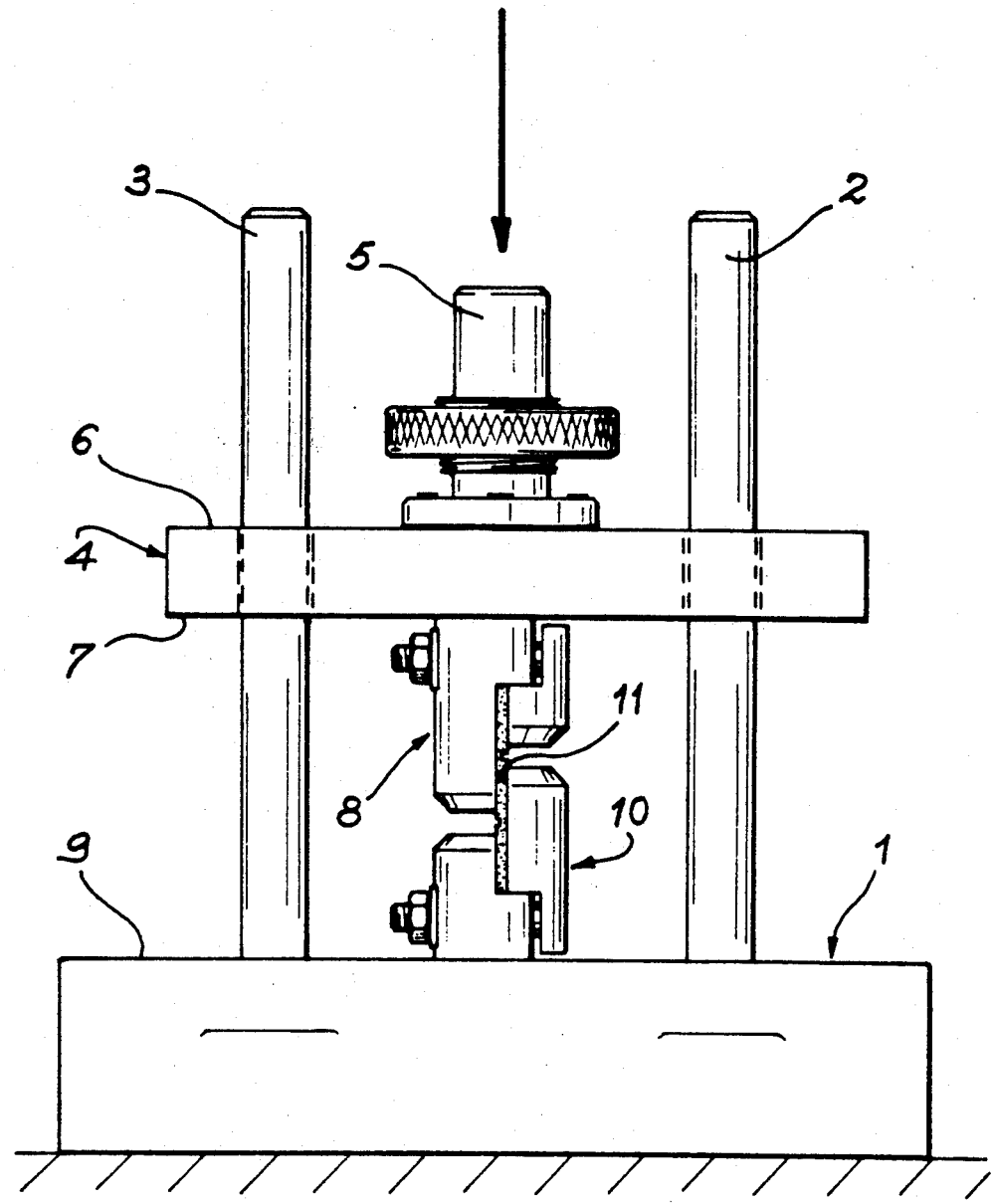

United States Patent [19]
Peres et al.

[11] Patent Number: 5,280,730
[45] Date of Patent: Jan. 25, 1994

[54] APPARATUS FOR THE COMPRESSIVE TESTING OF TESTPIECES FOR INTERLAMINAR SHEAR TESTS AND PROCESSES FOR THE SHEAR TESTING OF TESTPIECES, PARTICULARLY CURVED TESTPIECES

[75] Inventors: Patrick Peres, St. Médard en Jalles; Michel Cussac, La Teste, both of France

[73] Assignee: Aerospatiale Societe Nationale Industrielle, Paris, France

[21] Appl. No.: 847,573

[22] Filed: Mar. 5, 1992

[30] Foreign Application Priority Data

Mar. 8, 1991 [FR] France ................ 91 02835

[51] Int. Cl.⁵ ............................................ G01N 3/24
[52] U.S. Cl. .................................................. 73/846
[58] Field of Search ............ 73/815, 841, 842, 845, 73/846, 818-823, 825

[56] References Cited

U.S. PATENT DOCUMENTS

| 3,566,681 | 3/1971 | Iosipescu et al. ............ 173/841 |
| 4,916,954 | 4/1990 | Buzzard ....................... 73/845 |

FOREIGN PATENT DOCUMENTS

| 0300702 | 7/1988 | European Pat. Off. . |
| 55-31974 | 3/1980 | Japan . |
| 0091234 | 5/1985 | Japan ................... 73/818 |
| 0620869 | 8/1978 | U.S.S.R. ................ 73/845 |
| 474251 | 4/1982 | U.S.S.R. . |
| 979615 | 8/1985 | U.S.S.R. . |
| 125882 | 9/1986 | U.S.S.R. . |

OTHER PUBLICATIONS

American Society For Testing Materials, Phil. Pa. "Fatigue Of filamentary Composite Materials" ASTM Special Technical Publicatoin 636 By: Reifsnider pp. 122-139.

Experimental Mechanics Sep. 1975 "Continuous Servo-Controlled Alignment of Specimens In Materials Testing" By: A. Holmes pp. 358-364.

Primary Examiner—Robert Raevis
Attorney, Agent, or Firm—Hayes, Soloway, Hennessey & Hage

[57] ABSTRACT

Apparatus for testing testpieces (11) in the form of small plates, in which the testpiece is grasped between two pairs of jaws (12,13), which can be moved together. The jaws (12,13) are mounted on the platens (1,4) without hyperstaticity, which reduces the risks of introducing parasitic forces. The testpiece can be notched in such a way that its median portion is exposed to shear. The jaws then have adequate lengths to cover the principal faces of the testpiece (11) virtually up to the notches. The shear field is at a maximum and quasi-uniform in the median surface between the notches. This invention is useful for characterizing the interlaminar shear of plates made from composite materials and includes curved testpieces.

3 Claims, 4 Drawing Sheets

APPARATUS FOR THE COMPRESSIVE TESTING OF TESTPIECES FOR INTERLAMINAR SHEAR TESTS AND PROCESSES FOR THE SHEAR TESTING OF TESTPIECES, PARTICULARLY CURVED TESTPIECES

DESCRIPTION

The invention relates to an apparatus for the compressive testing of testpieces, which has two opposite lateral faces and which can, in the main presently envisaged application, be fragments of composite material plates, which have been notched in such a way as to have a median zone exposed to shear between the different layers from which the plates are made. The shear is referred to as interlaminar shear. It also relates to shear testing processes for test-pieces and in particular curved testpieces.

One way of keeping the testpieces between the compression platens of existing apparatuses consists of placing the ends of the notched testpieces in recesses of said platens, which is generally not satisfactory, as a result of the inevitable fitting inaccuracies, as well as the intrinsically asymmetrical behaviour of the notched testpiece necessarily leading to an inhomogeneity of the shear field in the median zone between the notches, so that the measurement of the material-representative shear stresses is falsified. Therefore the main object of the present invention is to supply a test-piece compressive testing apparatus, which is free from the deficiencies referred to hereinbefore and which makes it possible to obtain a quasi-uniform shear field.

The testpieces are compressed between two jaw or clamping systems, whereof each is constituted by two jaws. The jaws have a bearing surface of one of the lateral faces of the testpieces and one of the jaw also has an abutment surface of one end of the testpieces. Means are provided for moving together and apart the said jaws.

The apparatus can be improved if the jaws having an abutment surface are also provided with a cylindrical end fitting for fixing the jaw systems and a planar abutment face for the jaw systems. This reduces the risks of fitting inaccuracy resulting from a hyperstaticity of the apparatus.

It is recommended that the jaws of each jaw system be constructed with different lengths, so that their bearing surfaces extend substantially up to the surrounding of a median zone of the testpiece, where the shear is produced. A very good supporting of the testpiece is then obtained by the locking of the median zone between the long jaws. The bearing surface of one of the jaws can e.g. extend over a twice greater testpiece length than the bearing surface of the other jaw.

The bearing surfaces of the jaws are advantageously entirely in contact with the lateral faces of the testpiece and can thus be curved if the faces are also curved, so as to ensure a better behaviour of the testpieces and so as to reduce the compression bending and buckling risks.

The invention also relates to a process using such apparatuses for testpieces provided with two notches located on the lateral faces and surrounding a median zone of the testpieces.

It finally also relates to a process for the shear testing of curved testpieces provided on two opposite lateral faces with two notches surrounding a median zone of the testpiece. It consists of compressing the testpieces between the end faces joining the lateral faces, in which L designates the distance between the end faces, e the distance between the lateral faces and r the radius of curvature of the concave lateral face of the testpiece, the relations $r/L > 5$ and $L/e < 5$ being respected.

Figure 2:
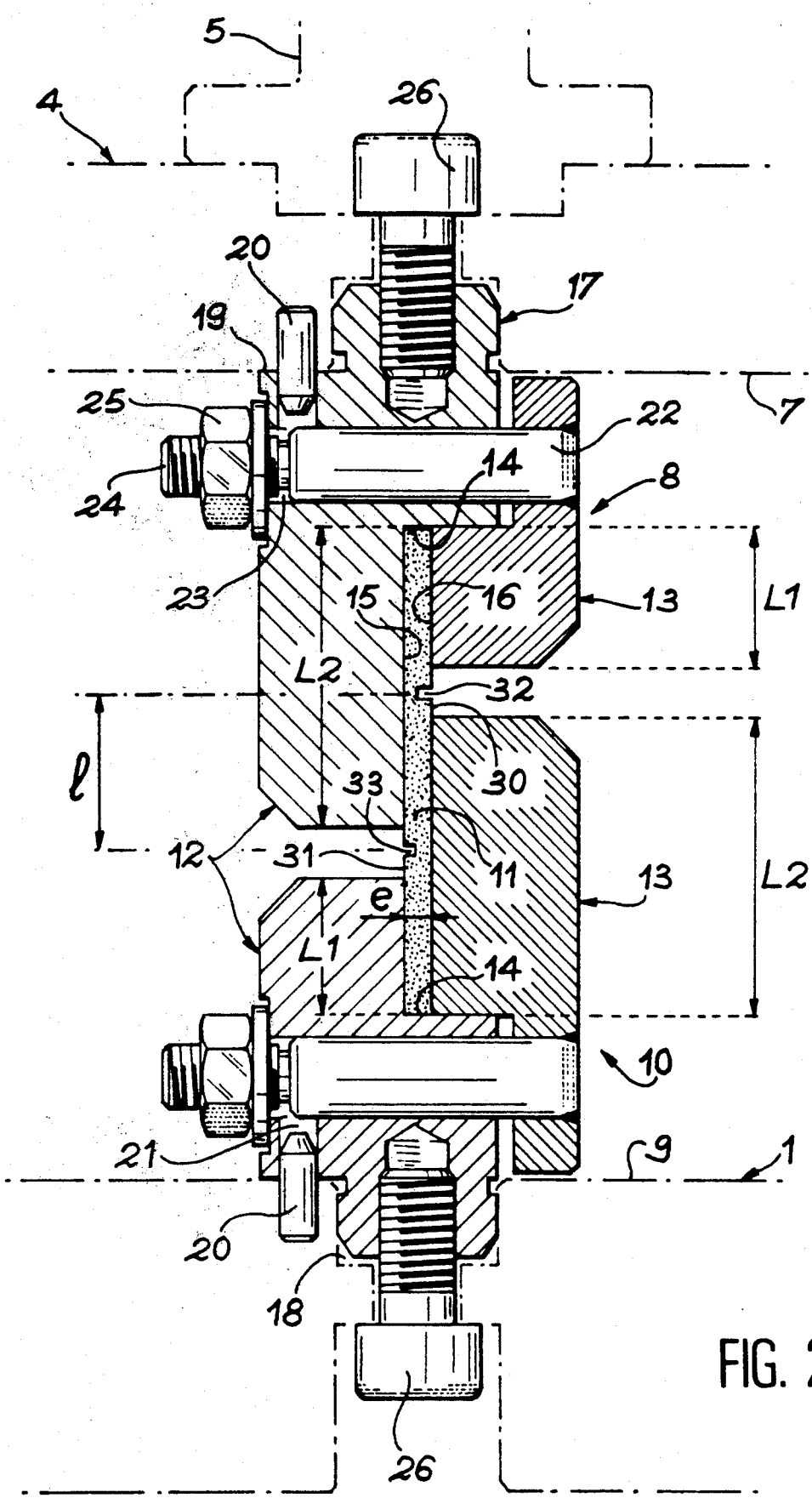
Figure 3:
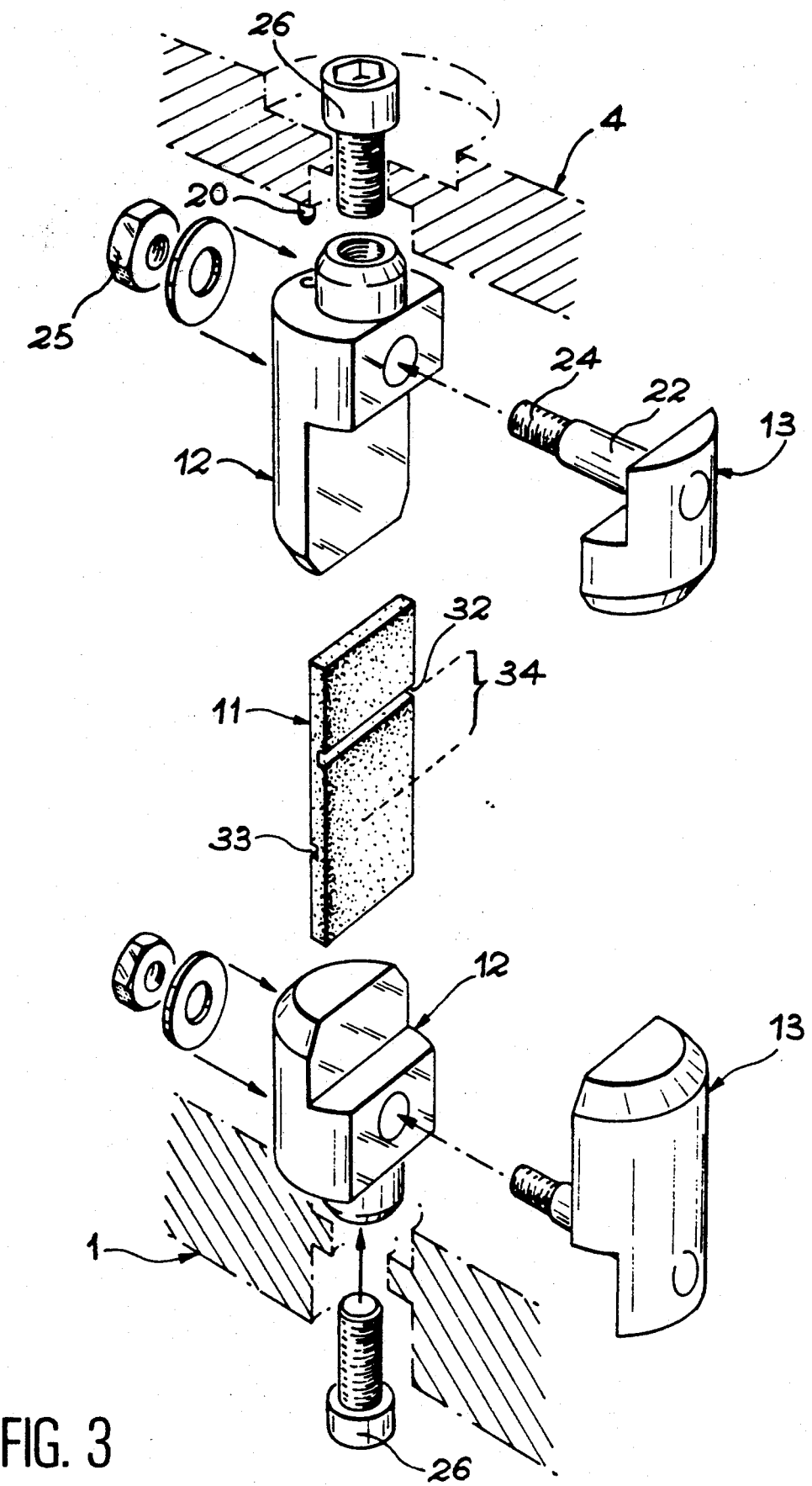
Figure 4:
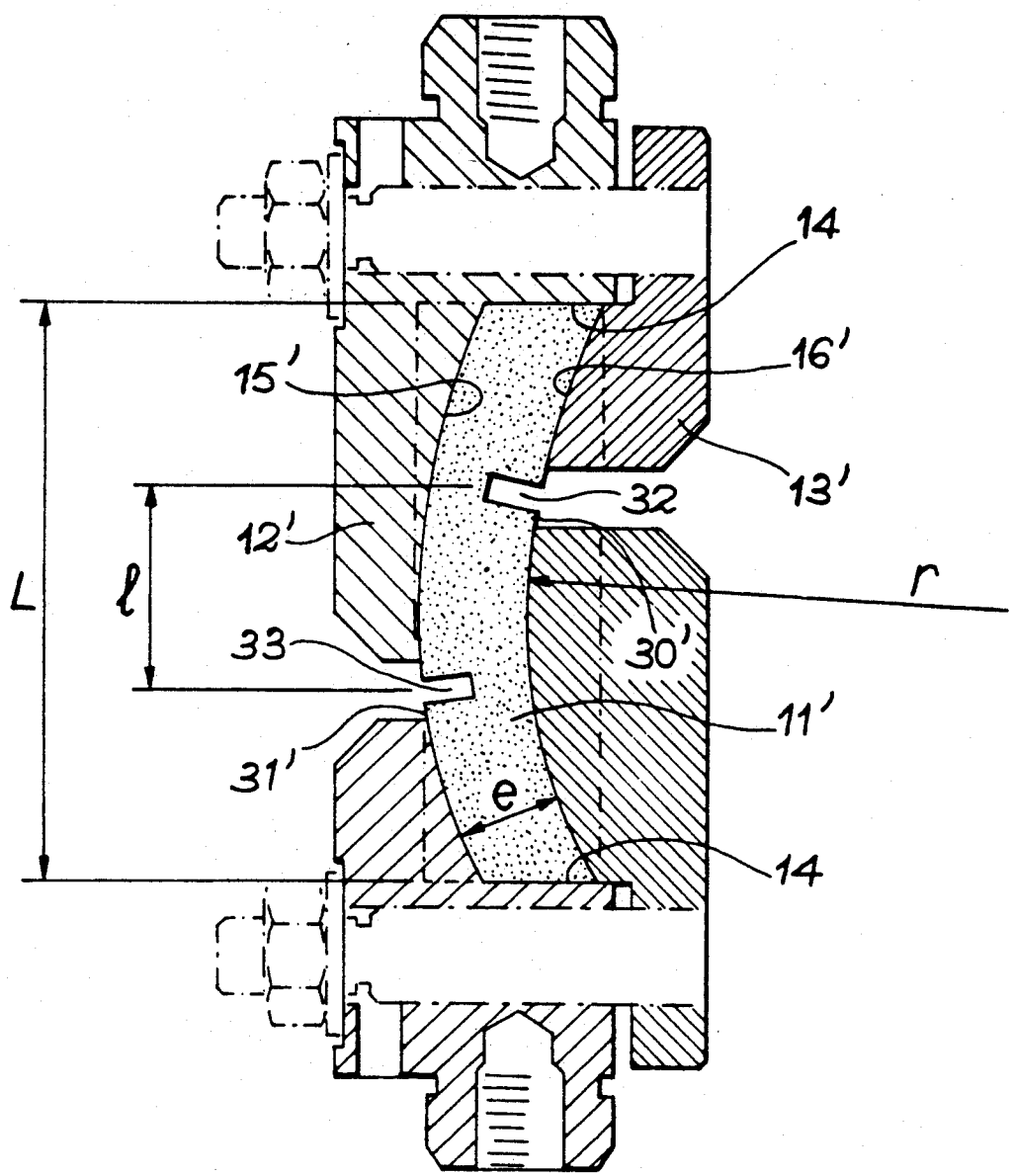

The invention is described in greater detail hereinafter relative to non-limitative embodiments and the attached drawings, wherein show:

FIG. 1 an overall view of the apparatus.
FIG. 2 the essential parts of the apparatus.
FIG. 3 the essential parts in an exploded view.
FIG. 4 in part another construction of the apparatus.

According to FIG. 1, the apparatus comprises a base 1, which is a fixed structure above which point two parallel columns 2 and 3, which penetrate openings in a platen 4, which they guide in a sliding movement. The openings are provided with not shown plain or ball bearings in order to ensure a reduced friction and clearance guidance. An end fitting 5 is fixed to an upper face 6, opposite to the base 1, of the platen 4. A not shown pressing means, which can be a jack or an inert weight, presses on the end fitting 5 and moves the platen 4 towards the base 1.

The lower face 7 of the platen 4, opposite to the preceding face, carries an upper jaw or clamping system 8 and the upper face 9 of the base 1 carries a lower jaw or clamping system 10. A testpiece 11 in the form of a plate is fixed between said jaw systems, whose construction will now be described with the aid of FIG. 2.

Each of them has an abutment jaw 12 and a locking jaw 13. Two facing abutment surfaces 14 are provided on the abutment jaws 12 and the testpiece 11 is compressed between them by its end surfaces. Each of the abutment jaws 12 and 13 also has a respective planar bearing surface 15 and 16 extending parallel to the compression direction and which bears integrally on one of the planar, opposite, lateral principal faces 30, 31 of the testpiece 11.

The abutment jaws 12 have a cylindrical end fitting 17 engaged in a recess 18 of the base 1 or the platen 4, as a function of the particular case and consequently serves to fix the jaw systems 8 and 10. It also has a planar face 19 perpendicular to the compression direction and which bears on the lower face 7 of the platen 4 or the upper face 9 of the base 1. This arrangement permits an installation of the jaw systems 8 and 10 with an adequate flexibility for ensuring that the testpieces 11 are received between the jaw systems without introducing parasitic bending or twisting forces. However, locating pins 20 are provided on the base 1 and the platen 4. They are located in a slot 21 of the respective abutment jaw 12 and make it possible to maintain the abutment jaws 12 substantially facing one another, in the same way as the locking jaws 13.

The locking jaws 13 have a rod 22 for penetrating a bore 23 of the associated abutment jaw 12. The rods 22 are terminated by a thread 24, which extends out of the abutment jaws 12 and around which a nut 25 is engaged. The tightening of the nut 25 moves together the jaws 12 and 13 and their bearing surfaces 15 and 16, which thus perfectly fit together the ends of the testpiece 11. Moreover, screws 26 make it possible to fix the abutment jaws 12 on the base 1 or the platen 4.

Each of the opposite faces 30 and 31 of the testpiece 11 has a notch, respectively 32 and 33, which weakens the cross-section of the testpiece 11 and extends over its entire width perpendicular to the compression direction. Thus, the notches 32 and 33 define a median zone 34 on the testpiece 11 (FIG. 3), where the shear develops in maximum and quasi-homogeneous manner at mid-height of the testpiece 11, because each of the notches 32,33 extends depthwise over half the said thickness (for an optimum width of approximately 0.5 mm). If the testpiece 11 is formed from a stack of composite material layers, it normally breaks at this point as a result of a breaking up of the assembly of layers. It is possible to deduce therefrom the interlaminar shear resistance of the material.

For all notched testpiece compression tests, it is recommended to have a length L between the notches 32 and 33 less than $\sigma/\tau \cdot e/2$, in which $\sigma$ and $\tau$ designate the shear and compression breaking stresses of the material and e the thickness of the testpiece 11. However, the length L must be sufficient for the test to be representative. It is considered that in the case of composite materials with a woven reinforcement architecture, it must cover at least three meshes.

The purity of the shear can be improved if the jaws 12 and 13 extend substantially up to the notch 32 or 33 on the principal face 30 or 31, on which the respective jaw bears. In the configuration shown, the locking jaw 13 of the lower jaw system 10 is consequently much longer than that of the upper jaw 8, whereas the abutment jaw 12 of the upper jaw system 8 is much longer than that of the lower jaw system 10. Therefore the median zone 34 is firmly maintained between the long jaws of the two jaw systems 8 and 10. In the represented configuration, the long jaws have a bearing surface 15 or 16 extending over a length L2 approximately twice greater than the length L1 of the bearing surface of the short jaws.

The apparatus is also advantageous in the case of shear-free, pure compression tests. Use is then made of testpieces having a similar shape, but without notches 32 and 33. The advantage of the apparatus is that it essentially prevents buckling in the median part 34 of the testpiece, as a result of the locking between the long jaws. Another arrangement shown in FIG. 4 shows that the test can also deal with curved testpieces 11'.

The modifications of the apparatus compared with the previous drawings consist in that the jaws 12' and 13' preferably have curved bearing surfaces 15' and 16', so that the opposite lateral faces 30' and 31' of the curved testpiece 11' bear over virtually their entire extent on the totality of the bearing surfaces 15' and 16'.

A better behaviour of the curved testpiece 11' is obtained in this way. Concave bearing surfaces 15' are the most useful due to the tendency to increase the curvature of curved testpieces 11' under compression, which leads to bending and disturbs the shear measurement.

In order to have a good quality of the results, it is recommended that use be made of curved testpieces 11', whose width (perpendicular to FIG. 4) is at least 5 mm and which roughly respect the relations $L/e<5$ and $r/L>5$, in which L designates the distance between the abutment surfaces 14, e the thickness of the curved testpiece 11' and r the radius of curvature of the concave lateral face 30' of the curved testpiece 11'. The notches 32,33 also extend up to the mid-thickness of the curved testpiece 11'.

As in the preceding case, the shear test is performed by compressing the end faces of the curved testpiece 11', which join the curved lateral faces 30' and 31', by abutment surfaces 14.

We claim:

1. Process for the shear testing of testpieces, comprising the use of a testing apparatus for testpieces having two opposite lateral faces, comprising two jaw systems between which the testpieces are compressed, each of said jaw systems comprising two jaws, each of said jaws having a bearing surface for bearing one of the respective lateral faces of the testpieces, means being placed on each of said jaw systems in order to move one of said jaws of each jaw system towards and away from the other of said jaws of the same jaw system, characterized in that one of the jaws of each jaw system also has an abutment surface for the testpieces, the testpieces being provided with two notches on the lateral faces and surrounding a median zone of the testpieces and being compressed between their end faces by the abutment surfaces.

2. Shear testing process according to claim 1, characterized in that the testpieces are curved.

3. Process for the shear testing according to claim 2, characterized in that it consists of compressing the testpieces between the end faces joining the lateral faces, in which L designates the distance between the end faces, e the distance between the lateral faces and r the radius of curvature of the concave lateral face of the testpiece, so that $r/L>5$ and $L/e<5$.

* * * * *